United States Patent [19]

Morais Cravador et al.

[11] Patent Number: 4,857,470

[45] Date of Patent: Aug. 15, 1989

[54] METHOD FOR THE PREPARATION OF BACTERIAL CLONES CARRYING OPTIMAL GENETIC INFORMATION FOR THE PRODUCTION OF THE FACTOR FOR RELEASE OF HUMAN GROWTH HORMONE IN *ESCHERICHIA COLI*

[75] Inventors: Alfredo J. Morais Cravador, Rhode St Genese; Paul Jacobs, Lanquesaint; Alex J. Bollen, Itterbeek; Ary Van Elsen, Brussels; Albert A. M. Herzog, Eppegem, all of Belgium

[73] Assignee: Smith Kline-RIT, s.a., Rixensart, Belgium

[21] Appl. No.: 689,679

[22] Filed: Jan. 8, 1985

[30] Foreign Application Priority Data

Jan. 12, 1984 [BE] Belgium ................................. 212201

[51] Int. Cl.4 .................. C12P 19/34; C12P 21/00; C07H 15/12; C12N 15/00
[52] U.S. Cl. ....................................... 435/320; 435/68; 435/70; 435/172.3; 435/317.1; 435/91; 536/27; 935/9; 935/29; 935/38; 935/57; 935/60; 935/72
[58] Field of Search ................. 425/70, 60, 172.3, 317, 425/172.1, 91, 253; 536/27, 324; 514/12; 935/9, 29, 38, 57, 60, 72, 320

[56] References Cited

U.S. PATENT DOCUMENTS

4,517,181  5/1985  Ling et al. ............................. 514/12

FOREIGN PATENT DOCUMENTS

0046039  2/1982  European Pat. Off. .............. 435/68

OTHER PUBLICATIONS

Barr et al. (1983), *Fed. Proceedings*, vol. 42, Abst. #1160, p. 1956.
Spiess et al., (1982), *Biochemistry*, vol. 80, pp. 5037–6040.
Gubler et al., *Proc. Nat'l Acad. Sci. USA*, vol. 80, pp. 4311–4314.
Soll et al., eds (1982), *The Applications of Computers to Research on Nucleic Acids*, IRL Press, Oxford and Washington, D.C., Narang, (1983), Tetrahedron, 39:3–22.

*Primary Examiner*—Thomas G. Wiseman
*Assistant Examiner*—S. Seidman
*Attorney, Agent, or Firm*—Edward T. Lentz; Janice E. Williams; Alan D. Lourie

[57] ABSTRACT

The DNA coding for human recombinant growth hormone releasing factor (GRF) cloned into a bacterial plasmid expression vector by assembling in one step selected synthetic DNA fragments.

1 Claim, No Drawings

METHOD FOR THE PREPARATION OF BACTERIAL CLONES CARRYING OPTIMAL GENETIC INFORMATION FOR THE PRODUCTION OF THE FACTOR FOR RELEASE OF HUMAN GROWTH HORMONE IN *ESCHERICHIA COLI*

FIELD OF THE INVENTION

The present invention relates to the preparation of bacterial clones carrying genetic information coding for the production of the factor for release of human growth hormone, selected with a view to optimizing expression of the factor in *E. coli* and to adapting itself to particular vectors of expression. More particularly, the present invention comprises a method for preparing a nucleotide sequence that expresses itself in an optimum manner in *E. coli;* the chemical synthesis of fragments of single stranded DNA representing the complete nucleotide sequence of the two DNA strands from the above-mentioned sequence; the hybridization of the strands and ligation of the strands to each other and to a plasmid vector; the cloning of the nucleotide sequence in *E. coli* and the selection and the characterization of clones bearing the information in question.

BACKGROUND OF THE INVENTION

The factor for release of the human growth hormone, also called somatocrinin, hereinafter designated by the abbreviation "GRF", is a positive regulator for the secretion of growth hormone, hereinafter designated by the abbreviation "GH". GRF is a polypeptide of 44 amino acids which has been sequenced and is isolated from a human pancreatic tumor causing acromeagaly. Antibodies against this peptide have enabled identification of an immunoreactive material in the hypothalamus of various primates; moreover, an apparently identical polypeptide has been isolated from the human hypothalamus. Finally, experiments of the "southern blot" type indicate that there is only a single gene coding for GRF. This, therefore, suggests that the tumoral pancreatic factor is coded by the same mRNA as the physiological hypothalamic factor. The usefulness of being able to produce abundant quantities of human GRF is due in particular to the fact that its genetic or physiological deficiency is a cause of dwarfism; that its stimulating effect on the synthesis of GH should lead to its usefulness in diagnosis of deficiencies or disorders of GH metabolism; that its administration could provide an acceleration in regeneration of tissues, for example, in the treatment of severe burn victims; and that it has been shown that the administration of human GRF to animals stimulates their growth.

SUMMARY OF THE INVENTION

Accordingly, one object of the present invention is the preparation of bacterial clones carrying the genetic information optimal for the production of GRF (hereinafter DNA-GRF) in *E. coli* from hybrid synthetic DNA fragments which are ligated and cloned in a host bacteria.

This and other objects are achieved in accordance with the present invention by providing a method of preparation of a bacterial clone carrying the optimum information for the production of GRF in *E. coli* comprising (1) determining from among the totality of DNA sequences potentially coding for GRF, a sequence that is optimal for the expression of GRF in *E. coli;*

(2) determining how to divide the sequence into single stranded fragments optimal for chemical synthesis of DNA and specificity requirements of hybrids to be formed between the DNA fragments;

(3) chemically synthesizing the fragments necessary to form a complete DNA-GRF;

(4) hybridizing and ligating said fragments in vitro in order to obtain DNA-GRF:

(5) inserting said DNA-GRF into a plasmid vector;

(6) transforming a host *E. coli* bacteria with the DNA-GRF plasmid vector;

(7) selecting from the transformed bacteria those which carry a plasmid so as to obtain a clone bank;

(8) isolating from said clone bank the clones carrying DNA-GRF by screening for DNA-GRF; and (9) characterizing said DNA-GRF by sequencing. A more particular embodiment of the present invention comprises:

(1) determinig from among the totality of sequences of DNA potentially coding for GRF, the sequence having the most codons corresponding to the codons most used by *E. coli* for each amino acid;

(2) determining how to divide the sequence into single stranded fragments in such a manner that hybrids desired between the DNA fragments have at least 10 nucleotides and the nondesirable hybrids have no more than 6 nucleotides;

(3) chemically synthesizing fragments of a size between 26 and 28 nucleotides, except for the and fragments of DNA-GRF;

(4) phosphonylating at the 5'-position all fragments which will not be directly bonded to a plasmid vector, and then hybridizing said chemically synthesized DNA fragments and ligating in vitro the hybridized fragments;

(5) inserting the hybridized and ligated fragments into a derivative of pBR 322 to obtain a product;

(6) transforming bacteria of strain *E. coli* ATCC 31446 with the product of step 5;

(7) selecting clones of the bacteria which carry a plasmid by means of antibiotic resistance;

(8) isolating clones carrying the DNA-GRF from the selected clones through hybridization with constituent fragments of DNA-GRF labelled with $^{32}P$; and (9) characterizing the DNA-GRF by sequencing by means of the Maxam and Gilbert method from a restriction site close to DNA-GRF in the plasmid.

DETAILED DESCRIPTION OF THE INVENTION

The method for preparation of a bacterial clone carrying the optimum genetic information for production of the factor for release of human growth hormone in *Escherichia coli* is characterized by the combination and the selection means detailed below.

(a) The definition of the optimum DNA sequence for the production of human GRF by *E. coli* can be made, for example, by selecting for each amino acid to be encoded the most frequently used triplet in the bacteria. The use of codons in *E. coli* is described in "Ikemura, T., Nucleic Acid Research 11, 143–144 (1982)" and "Gouy, P. and Goutier, C., Nucleic Acid Research 10, 7055–7084 (1982)". Both references are incorporated herein by reference. The possibilities of non-desirable hybridization between fragments can also be taken into account by changing some of the involved bases without changing the encoded amino acids.

(b) The double stranded DNA sequence defined by the method described in (a) can only be obtained by chemical synthesis of single stranded DNA fragments. The cleaving of the complete sequence into its constituent fragments must, in particular,, meet the following criteria: it must be such that the single stranded segments are of a size compatible with the current state of the art of chemical synthesis of DNA. This means not longer than about 30 bases. The state of the art is described in "Narang, S. A., Tetrahedron 39, 3–22, 1983", incorporated herein by reference.

The fragments are preferably selected such that only the anticipated hybridizations can occur. This can be determined a priori by computer by determining all the possible hybridizations between fragments and subfragments. Numerous computer programs exist for this purpose. The state of the art in this field can be found in "The Applications of Computers to Research on Nucleic Acids" (Soll, D. and Roberts, R. J. eds., IRL Press, Oxford and Washington, D.C., 1982) incorporated herein by reference.

(c) The chemical synthesis of DNA can take place using various methods which are described in "Narang, S. A. Tetrahedron 39 (1983) 3–22; Itakura, K., IBS (1982) 442–445; Ohtruka, E., Ikehara, M. and Soll D., N.A.R. 10 (1982) 6553–6570", all incorporated herein by reference.

For example, the phosphotriesters method described by Brown, EL. L; Belagaje, R., Ryan, M. J. and Khorana, H. G. (Methods in Enzymology 68 (1979) 109), or the phosphite triesters method described by Letsinger, R. L. and Lunsford, W. B. (J. Am. Chem. Soc. 98 (1976) 3655), all incorporated herein by reference, can be used.

These methods vary in the degree of oxidation of the phosphorus atom in the nucleotide intermediaries used during the coupling reaction.

The synthesis can take place either in the liquid phase or on a solid support; when synthesis is on a solid support, various supports are possible, for example, silica, polystyrene balls, or glass balls. The use of these supports is described in Izo, H., Ike, Y., Ikuta, S. and Itakura, K. (Nucleic Acid Research 10 (1982) 1755); Efimov, V. A., Reverdato, S. V. and Chakhmakhcheva, O. G., Nucleic Acid Research 10 (1982) 6675; Hattar, J. B., Rayner, B. and Imbach, J. L., Nucleosides and Nucleotides 1 (1982) 289, all incorporated herein by reference.

(d) The hybridization and ligation of the synthetic DNA fragments with each other can be carried out by various methods which are described in Molecular Cloning (1982 - Maniatis, T., Fritsch, E. F. and Sambrook, J., CSH Publ.), incorporated herein by reference. These methods are based on the principle of hybridization of complementary DNA sequences. They consist of mixing the DNA fragments under temperature and ionic strength conditions which are adequate for the formation of specific hybrids. The ligation of these hybridized fragments is the result of the action of an enzyme, for example, T4 DNA ligase.

(e) The in vitro formation of hybrid molecules between the double stranded DNA to be cloned and the DNA of plasmid vectors is carried out using the method described in Molecular Cloning (1982 Maniatis, T., Fritsch, E. F. and Sambrook, J., CSH Publ.), incorporated herein by reference. The method comprises mixing molecules under appropriate temperature and ionic strength conditions. The method of Maniatis was the protocol which was used in the present invention. The DNA vector used in the in vitro reaction to insert the hybrids can come from various plasmids. Among the most commonly used plasmids are the pBR322 plasmid which contains two possible insertion sites, PstI and BamHI. These two sites are suitable for the insertion of the above-mentionned DNA (Bolivar, F., Rodriguez, R. L., Greene, P. J., Betlach, M. C., Heynecker, H. L., Boyer, H. W., Crosa, J. H. and Falkow, S., Gene 2 (1977) 95) incorporated herein by reference. The derivatives of the pBR322 plasmid are also suitable. In carrying out this invention, for example the PCQV2 plasmid (Queen, C., J. of Mol. and Applied Genet. 2, 1–10, 1983), incorporated herein by reference, in which cloning takes place at the BamHI site, is used. The cohesive ends of single stranded DNA thus generated are then digested by means of an enzyme, for example, Mungbean nuclease.

(f) The majority of methods used for transforming bacteria using exogenous DNA call for particular treatment of the bacteria with calcium chloride, and aim at optimizing the effeciency of the transformation for various strains of bacteria. Within the framework of the invention, several types of bacteria can act as hosts for the vector used, preferably those whose growth conditions are particularly pratical, for example E. coli K12 strain M294 (ATCC 31446), E. coli B and E. coli X 1776 (ATCC 31537).

In addition, the transformation is selected from among the various methods of transformation, described in Mandel, M. and Higa, A. (1970, J. Mol. Biol. 53, 154), incorporated herein by reference.

(g) Due to the markers for resistance to antibiotics present in the DNA of the vector, it is straight forward to isolate the bacteria transformed by the recombined DNA in vitro. For example, if the DNA of the vector carries the TetR gene, any bacteria carrying such a vector will be resistant to tetracycline. In addition, if the insertion of the DNA into the vector has the effect of inactivating a gene resistant to an antibiotic, the bacteria which carry the recombinant vector will be detected by their sensitivity to this antibiotic. For example, the AmpR character of the PCQV2 plasmid is selected as the label of choice.

(h) The screen for selection of the cloned carriers of DNA-GRF can be carried out by methods using either a synthetic probe or immunological techniques. These various approaches are detailed in Genetic Engineering, Vol. 1, Williamson, R., Eds. (1981) Academic Press, New York, incorporated herein by reference. Within the framework of the present invention, preferably one or several of the constituent fragments on DNA-GRF are used as oligodesoxyribonucleotide probe labelled with $^{32}P$ which is hybridized with the clones from the bank.

(i) The DNA sequences created in one or several of the clones obtained can be characterized by sequencing methods described in Maxam, A. and Gilbert, W., Methods in Enzymology 65 (1980) 197–559 and in Sanger, F., Nicklen, S. and Coulson, A. R., Proc. Natl. Acad. Sci. USA 74 (1977) 5463, all incorporated herein by reference. Within the framework of the present invention, the Maxam and Gilbert method is preferably selected.

EXAMPLE

The following non-limiting example which applies to the cloning of DNA-GRF in the PCQV2 plasmid will enable better understanding of the invention.

1. Determining the Optimal Sequence for the Expression of GRF in *E. coli*

The sequences potentially coding for GRF are extremely numerous due to the degeneracy of the genetic code. Within the frameword of the present invention, we have selected a sequence such that the 44 amino acids are each encoded by the most frequently used codon in *Escherichia coli* for that amino acid.

The invented sequence is the following:

```
5' TACGCTGACGCTATCTTCACTAACTCTTACCGTAAAGTTCTGGGTCAGCTG
3' ATGCGACTGCGATAGAAGTGATTGAGAATGGCATTTCAAGACCCAGTCGAC
5' TCTGCTCGTAAACTGCTGCAGGACATCATGTCTCGTCAGCAGGGTGAATCT
3' AGACGAGCATTTGACGACGTCCTGTAGTACAGAGCAGTCGTCCCACTTAGA
5' AACCAGGAACGTGGTGCTCGTGCTCGTCTGTAAG 3'
3' TTGGTCCTTGCACCACGAGCACGAGCAGACATTCAGCT 5'
```

It is further characterized in that (1) its 5' ends (on the noncoding strand, i.e., the strand corresponding to the mRNA sequence) is "blunt" and corresponds to the first nucleotide of the second codon of GRF and (2) its 3' end on the coding strand) finishes in phase after the triplet coding for the last amino acid of GRF, with a triple "stop" (TAA), which itself is followed by the part of a SalI restriction site as it appears after cleaving of a DNA by SalI.

2. Determining how to divide the Sequence into Single Stranded DNA Fragments

Division of the sequence into single stranged fragments, which are suitable for chemical synthesis and which are adapted to the requirements of a nonambiguous reconstitution of DNA-GRF by hybridizaton and bonding, can be done in various ways. Within the framework of the present invention, division of the strand into the following fragments is preferred

```
A27:5' TACGCTGACGCTATCTTCACTAACTCT
B27:5' TACCGTAAAGTTCTGGGTCAGCTGTCT
C27:5' GCTCGTAAACTGCTGCAGGACATCATG
D27:5' TCTCGTCAGCAGGGTGAATCTAACCAG
E28:5' GAACGTGGTGCTCGTGCTCGTCTGTAAG
F14:5' ATAGCGTCAGCGTA
G27:5' AGAACTTTACGGTAAGAGTTAGTGAAG
H27:5' AGCAGTTTACGAGCAGACAGCTGACCC
I26:5' CCTGCTGACGAGACATGATGTCCTGC
J27:5' GAGCACCACGTTCCTGGTTAGATTCAC
K19:5' TCGACTTACAGACGAGCAC
```

3. Synthesis of Single Stranded DNA Fragments Constituting to DA-GRF Fragments

The synthesis of the F14 fragment was carried out on a solid polystyrene support using a monomer and six protected dimers prepared in solution by a combination of different described or modified methods. The other fragments were synthesised on a mixed polydimethylafragments crylamide-silica in a column under continuous flux in accordance with the method described by Gait, M. J., Matthes, H. W. D., Sing, M. and Titmas, R. C. (J. Chem. Soc. Chem. Comm. p 37, 1982), incorporated herein by reference, by using only dimers or a monomer and dimers depending on whether the fragment contained an odd or even number of deoxyribonucleotides.

The deoxyribonucleotides carrying the protective dimethoxytrityl group were first purified on Sephadex G-50 by elution with $10^{-2}M$ pH 7.0 and then twice with HPLC on a Radial Pak RPH C18 10 μm column before and after deprotection, by using TEAA 50 mM pH 7 plus acetonitrile as an eluent and gradients of 15% to 30% of acetonitrile achieved in 20' and 0% to 20% of acetonitrile achieved in 20', respectively, and a flow of 2 ml/min. The final obtained were on the order of 8%.

4. Hybridization and Bonding

Bonding with the T4 DNA ligase of the hybridized DNA fragments necessitates that the fragments be phosphorylated on their 5' end. Within the framework of the present invention, this is preferably done with T4-polynucleotide kinase. Various methodes are described in "Molecular Cloning" (Maniatis, T., Fritsch, E. F., Sambrook, J., CSH, ed. 1982), incorporated herein by reference.

Preferably, the following protocol is used: to 100 picomoles of each lyophilized deoxyoligonucleotide were added 2 μl of ATP 0.1 mM; 2 μ of $^{32}P$ ATP 3.3 nM with 3000 Ci per mM; 3,μl of Tris HCl buffer 660 mM pH 7.8, MgCl$_2$ 66 mM, mercaptoethanol 260 mM; 5 units of T4 polynucleotide kinase, which is 0.5 μl and 22.5 μl of water. The reaction mixture was incubated for 1 hour at 37° C., then fractionated on a column of 5 ml of Sephadex G50.

The fractions containing the labelled DNA were collected, lyophilized and resuspended in water. The A and K fragments were preferably not phosphorylated in order to avoid the formation of DNA-GRF polymers.

Fifty pmoles of each fragment were mixed, lyophilized and resuspended in 49.5 μl of Tris HCl buffer 50 mM 7.4, MgCL$_2$ 10 mM, dithiothreitol (DTT) 10 mM, spermidine 1 mM. The mixture was heated at 90° C. for 2' then cooled slowly at 4° C. Then 1 μl of ATP 50 mM, 0.5 μl of bovine serum albumin (BSA) at 10 mg/ml and 10μ which is 10 μl of T4 DNA ligase were added.

The mixture was incubated for 25 hours at 16° C. The product may be purified, preferably by fractionation on a 7.5 % acrylamide gel and eluting a zone which corresponds to a DNA of an expected size. In this case the expected size is approximately 140 base pairs.

5. In Vitro Synthesis of Recombinants Between the DNA-GRF and the DNA of the PCQV2 Vector The insertion of the DNA-GRF into the PCV2 plasmid necessitates the preparation of the vector such that it presents a start translation signal (ATG) wherein the G is the last base of a "Blunt" end and wherein the other end is the remaining section of a SalI restriction site produced by cleaving the vector with SalI.

The state of the art in the production of this step can be found in "Molecular Cloning" (Maniatis, T., Fritsch, E. F., Sambrook, Jr., CSH Ed. 1982), incorporated herein by reference.

One hundred ng (which is 0.033 picomoles) of the vector prepared as described were mixed with the DNA-GRF. The two were ligated as described in step 4.

6. The Cloning of the MM294 *Escherichia coli* Strain

The transformation of the MM294 strain was then carried out ("Molecular Cloning", Maniatis, T., Fritsch, E. F., Sambrook, J., CSH Ed. 1982), incorporated herein by reference, wherein the restriction system was modified so as to tolerate the presence of a foreign DNA in accordance with the method described in "Molecular Cloning" (Maniatis, T., Fritsch, E. C., and Sambrook, J., CSH Ed. 1982), incorporated herein by reference.

7. Obtaining the Clone Bank Due to the $Amp^R$ character of the plasmid, the transformed bacteria can be selected by growth on a medium containing ampicillin.

The totality of the steps described above yielded a bank of 1500 clones, of which a large part contained DNA sequences coding for GRF.

8. Isolation of Clones Carrying DNA-GRF

Clones carrying DNA-GRF were detected by using the B27 and J27 fragments as a probe. After having labelled these probes with $^{32}P$ by an enzymatic reaction (kination at 5' end of the probe), the probes were used to screen the clone bank. The DNA of each clone was fixed on a sheet of nitrocellulose, using the technique of Grunstein, M. and Hogness, D. (Proc. Natl. Acad. Sci USA 72 (1975) 3961), incorporated herein by reference, and the DNA was hybridized with the synthetic probe labelled with $^{32}P$. Under appropriate ionic and temperature conditions (0.9 M NaCl and 50° C.), the radioactive probe will specifically recognize the DNA of the clones carrying a homologous sequence, that is, a sequence of nucleotides typical of DNA-GRF. The positive clones were visualized by autoradiography. This method enabled the identification of 79 clones (out of 1500 analyzed) carrying all or part of the DNZ-GRF.

9. Characterization of the DNA-GRF of the pULB1323 Clone

The DNA-GRF of the pULB1323 was characterized by confirming its nucleotide sequence. For this purpose, the DNA of the recombinant plasmid is prepared an the cleaved at the sing AaII restriction site in the recombinant plasmid. The ends of the linearized plasmid are then labelled with $^{32}P$. The plasmid is then cut with the EcoRI enzyme generating two fragments, one of which carries the DNA-GRF at its labelled end. The labelled fragment is then subjected to a series of chemical reaction leading to the production of labelled oligonucleotides, of different sizes, whose analysis on polyacrylamide gel leads to confirmation of the sequence of bases in accordance with the technique of Maxam, A. M. and Gilbert, W. (Poc. Natl. Sci. USA 74 (1977) 560), incorporated herein by reference. The DNA-GRF corresponded perfectly to the sequence defined in step 1.

While the invention has been described in detail, and with reference to specific embodiments thereof, it will be apparent to one skilled in the art that various changes and modifications can be made there without departing from the spirit and scope thereof.

We claim:

1. A method for preparing a DNA vector having a coding sequence for growth hormone releasing factor ("GRF") which comprises hybridinzing and ligating the chemically synthesized DNA sequences A27, B27, C27, D27, E28, F14, G27, H27, I26,J27 and K19 to prepare a sequence coding for GRF and inserting the sequence into a plasmid vector.

* * * * *